(12) United States Patent
Kojima et al.

(10) Patent No.: US 9,778,186 B2
(45) Date of Patent: Oct. 3, 2017

(54) SYSTEM FOR ELECTRON BEAM DETECTION

(71) Applicant: KLA-Tencor Corporation, Milpitas, CA (US)

(72) Inventors: Shinichi Kojima, Cupertino, CA (US); Hamada Wahba, San Jose, CA (US); Michael R. Gluszczak, San Jose, CA (US); Joseph A. DiRegolo, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 139 days.

(21) Appl. No.: 14/686,308

(22) Filed: Apr. 14, 2015

(65) Prior Publication Data

US 2016/0011110 A1 Jan. 14, 2016

Related U.S. Application Data

(60) Provisional application No. 61/979,774, filed on Apr. 15, 2014.

(51) Int. Cl.
*H01J 37/22* (2006.01)
*G01N 21/64* (2006.01)
*H01J 37/244* (2006.01)

(52) U.S. Cl.
CPC .......... *G01N 21/64* (2013.01); *H01J 37/226* (2013.01); *H01J 37/244* (2013.01);
(Continued)

(58) Field of Classification Search
CPC .... G01T 1/20; G01T 1/24; G01T 1/17; G01T 1/2002; H01J 37/226; H01J 37/244;
(Continued)

(56) References Cited

U.S. PATENT DOCUMENTS 6,534,773 B1 * 3/2003 Iwanczyk ............. G01T 1/2018
250/370.11
7,714,287 B1 * 5/2010 James .................. H01J 37/1472
250/306

(Continued)

OTHER PUBLICATIONS

International Search Report for Application No. PCT/US2015/025930, Dated Jul. 14, 2015, 3 pages.

*Primary Examiner* — David E Smith
(74) *Attorney, Agent, or Firm* — Suiter Swantz pc llo

(57) ABSTRACT

An electron beam detection apparatus includes a first aperture element including a first set of apertures. The apparatus includes a second aperture element including a second set of apertures. The second set of apertures is arranged in a pattern corresponding with the pattern of the first plurality of apertures. The detection apparatus includes an electron-photon conversion element configured to receive electrons of the electron beam transmitted through the first and second aperture elements. The electron-photon conversion element is configured to generate photons in response to the received electrons. The detection apparatus includes an optical assembly including one or more optical elements. The detection apparatus includes a detector assembly. The optical elements of the optical assembly are configured to direct the generated photons from the electron-photon conversion system to the detector assembly.

39 Claims, 12 Drawing Sheets

(52) U.S. Cl.
CPC . *H01J 2237/043* (2013.01); *H01J 2237/2443* (2013.01); *H01J 2237/2446* (2013.01); *H01J 2237/24578* (2013.01)

(58) Field of Classification Search
CPC ............... H01J 37/3171; H01J 37/3174; H01J 2237/043; H01J 2237/2443; G01N 21/00; G01N 21/64
See application file for complete search history.

(56) References Cited

U.S. PATENT DOCUMENTS

| | | |
|---|---|---|
| 8,692,204 B2 | 4/2014 | Kojima et al. |
| 2009/0294665 A1 | 12/2009 | Koike et al. |
| 2010/0084553 A1* | 4/2010 | Frosien .................... G01T 1/00 250/307 |
| 2010/0117001 A1 | 5/2010 | Looije |
| 2010/0237251 A1 | 9/2010 | Tonami et al. |
| 2010/0320382 A1* | 12/2010 | Almogy .................. H01J 37/05 250/307 |
| 2012/0273686 A1* | 11/2012 | Kojima ................ H01J 37/244 250/362 |
| 2013/0157198 A1* | 6/2013 | Yoshikawa ........... G03F 7/2059 430/296 |
| 2013/0234032 A1 | 9/2013 | Wang et al. |
| 2014/0158907 A1* | 6/2014 | Hamochi ................ H01J 37/26 250/442.11 |
| 2014/0350394 A1* | 11/2014 | Niedre ................ A61B 5/0071 600/426 |

* cited by examiner

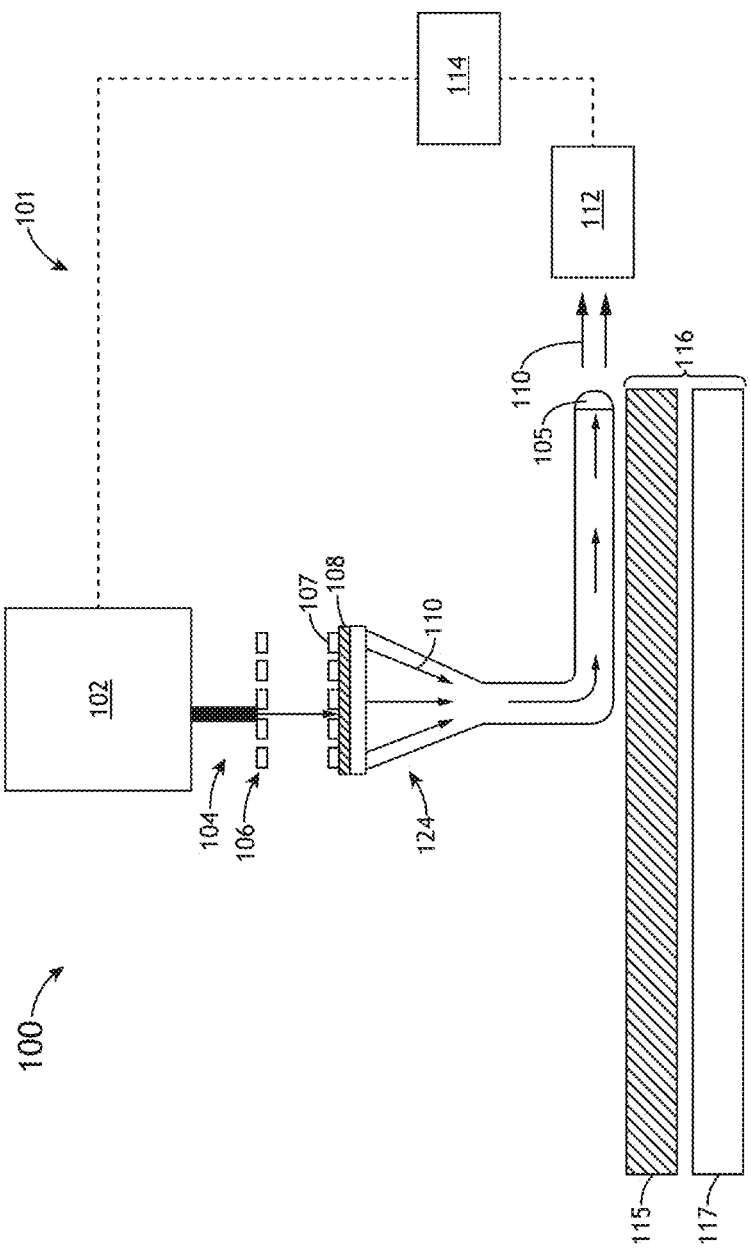

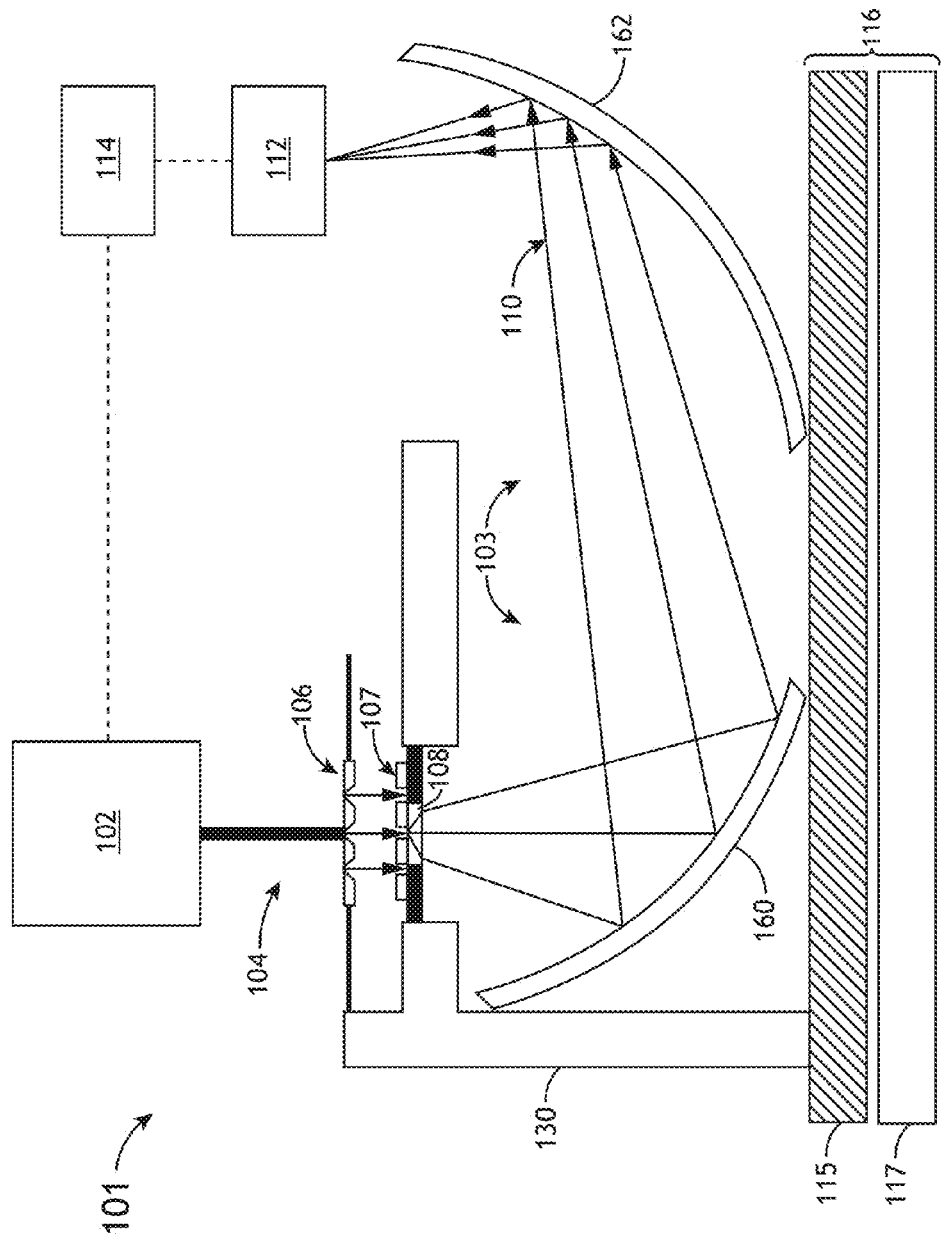

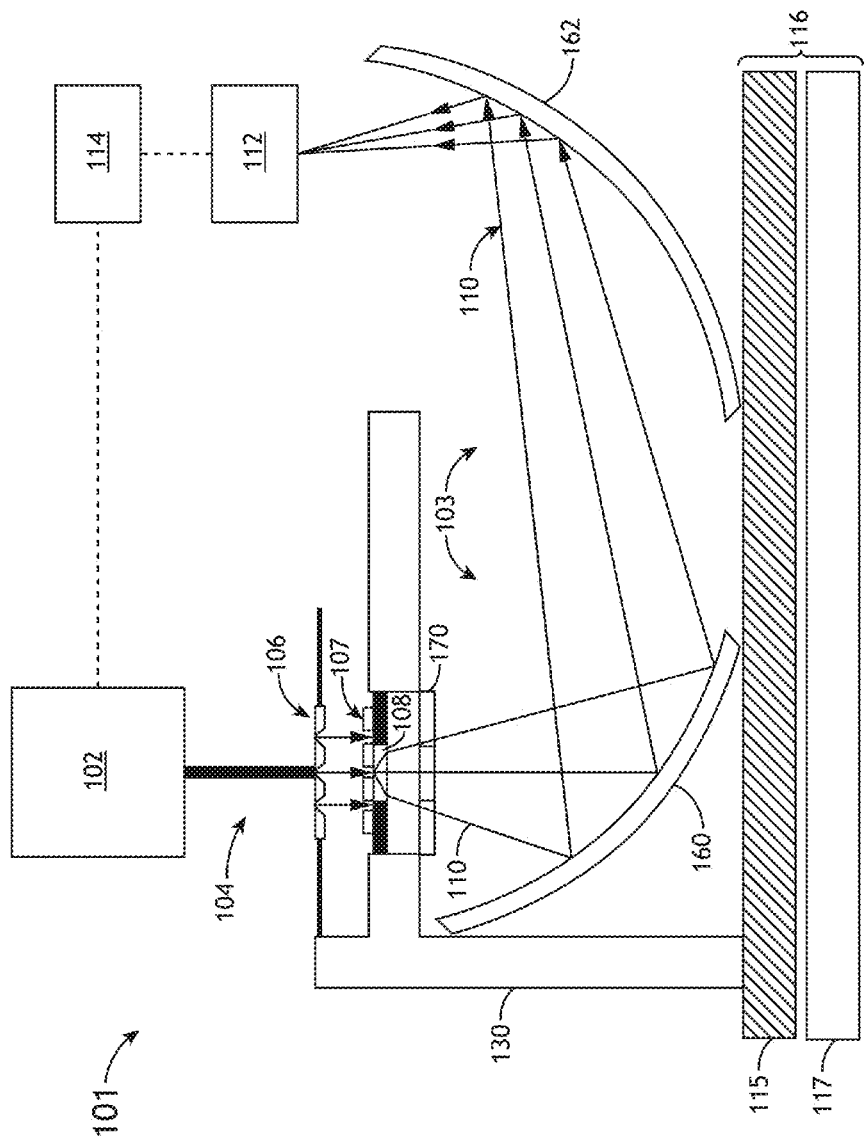

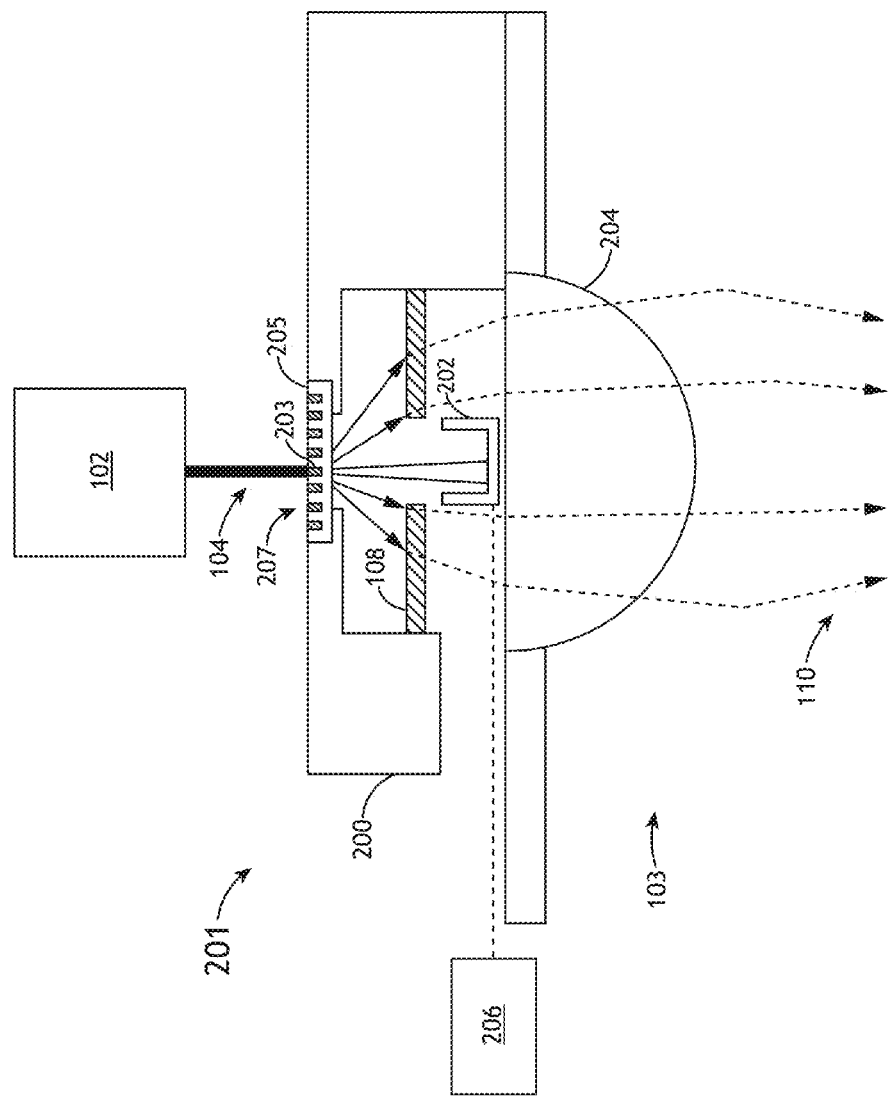

SYSTEM FOR ELECTRON BEAM DETECTION

CROSS-REFERENCE TO RELATED APPLICATION

The present application claims the benefit under 35 U.S.C. §119(e) of U.S. Provisional Application Ser. No. 61/979,774, filed Apr. 15, 2014, entitled ELECTRON BEAM DETECTION METHOD APPLICABLE TO ELECTRON BEAM LITHOGRAPHY AND INSPECTION SYSTEMS, naming Shinichi Kojima, Hamada Wahba, Michael Gluszczak and Joseph DiRegolo as inventors, which is incorporated herein by reference in the entirety.

This invention was made with government support under Grant No. HR0011-07-9-0007 awarded by DARPA. The government has certain rights in this invention.

TECHNICAL FIELD

The present disclosure generally relates to electron beam detection, and, more particularly, to an electron beam detection apparatus positioned proximate to a sample stage.

BACKGROUND

The demand for integrated circuits having ever-small device features continues to increase. As a result, the need for improved electron beam instruments used in the fabrication of integrated circuits continues to grow. Electron beam instruments used in the fabrication of devices may include instruments such as an electron beam lithography tool or an electron beam inspection or review tool. Electron beam instruments often utilize beam detection devices to measure the position or other characteristics of the given electron beam. Commonly implemented electron beam detection approaches are limited due to various mechanical constraints of currently utilized systems. Therefore, it would be advantageous to provide an improved apparatus, system and/or method to cure the defects such as those identified above.

SUMMARY

An apparatus for electron beam detection is disclosed, in accordance with another illustrative embodiment of the present disclosure. In one illustrative embodiment, the apparatus includes a first aperture element including a first plurality of apertures. In another illustrative embodiment, the apparatus includes a second aperture element including a second plurality of apertures. In another illustrative embodiment, the second plurality of apertures is arranged in a pattern corresponding with the pattern of the first plurality of apertures. In another illustrative embodiment, the apparatus includes a scintillator element configured to receive electrons of the patterned electron beam transmitted through the first aperture element and the second aperture element. In another illustrative embodiment, the scintillator element is configured to generate light in response to the received electrons. In another illustrative embodiment, the apparatus includes an optical guide assembly. In another illustrative embodiment, the apparatus includes a light detector configured to measure a light signal from the scintillator element. In another illustrative embodiment, the optical guide assembly is configured to direct light generated by the scintillator element to the light detector.

An apparatus for electron beam detection is disclosed, in accordance with another illustrative embodiment of the present disclosure. In one illustrative embodiment, the apparatus includes a scattering element including a plurality of pillar structures configured to scatter electrons of the electron beam. In another illustrative embodiment, the apparatus includes a scintillator element configured to receive electrons scattered from the plurality of pillar structures of the scattering element. In another illustrative embodiment, the scintillator element is configured to generate light in response to the received scattered electrons. In another illustrative embodiment, the apparatus includes an optical guide assembly. In another illustrative embodiment, the apparatus includes a light detector configured to measure a light signal from the scintillator element, wherein the optical guide assembly is configured to direct light generated by the scintillator element to the light detector.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 1D is a schematic view an electron beam detection assembly, in accordance with one embodiment of the present disclosure.

FIG. 1J is a schematic view an electron beam detection assembly, in accordance with one embodiment of the present disclosure.

FIG. 1K is a schematic view an electron beam detection assembly, in accordance with one embodiment of the present disclosure.

FIG. 2 is a schematic view an electron beam detection assembly, in accordance with one embodiment of the present disclosure.

DETAILED DESCRIPTION OF THE INVENTION

Reference will now be made in detail to the subject matter disclosed, which is illustrated in the accompanying drawings.

Figure 1A:
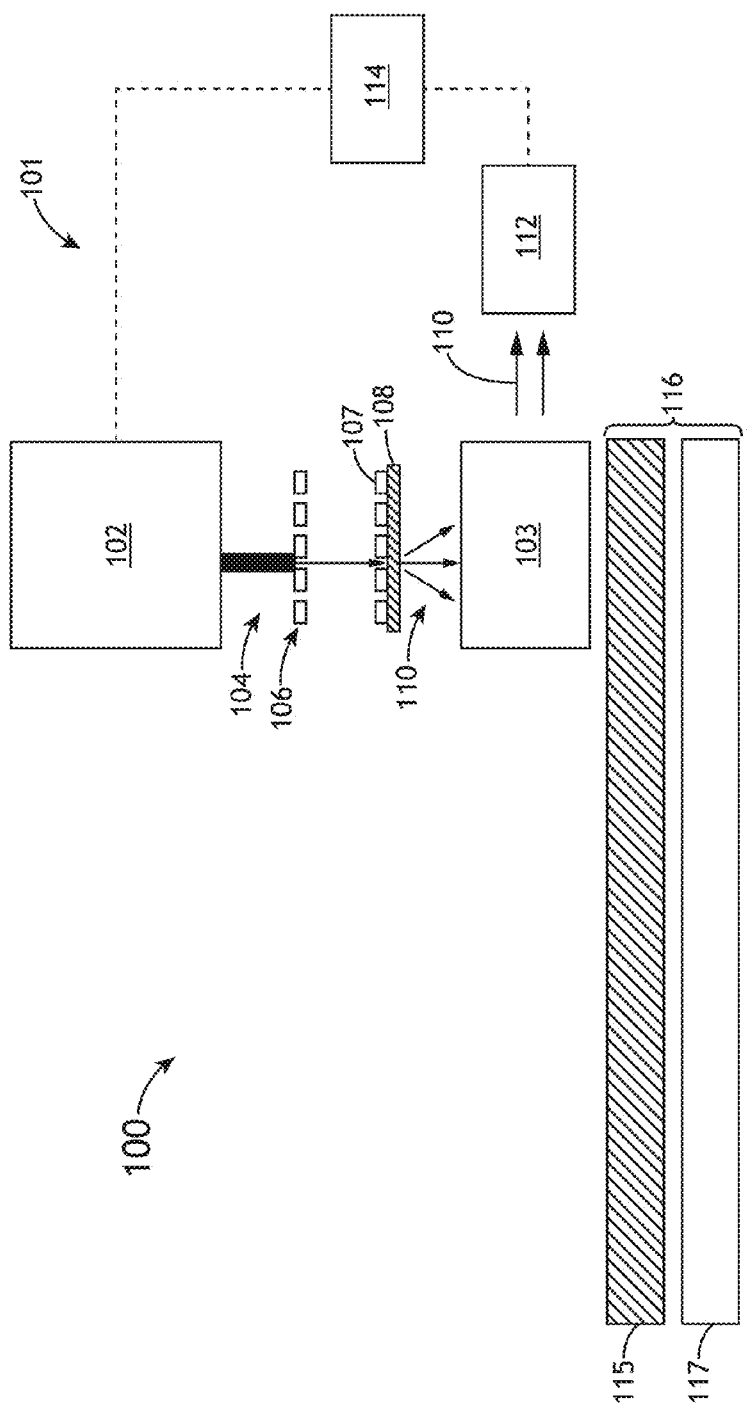
FIG. 1A is a schematic view an electron beam detection assembly, in accordance with one embodiment of the present disclosure.

Referring generally to FIGS. 1A through 2, a system 100 equipped with an electron beam detection assembly 101 is described in accordance with one or more embodiments of the present disclosure. The detection of an electron beam is described in U.S. Pat. No. 8,692,204 to Kojima et al., entitled "Apparatus and Methods for Electron Beam Detection," issued on Apr. 8, 2014, which is incorporated herein by reference in the entirety.

Figure 1B:
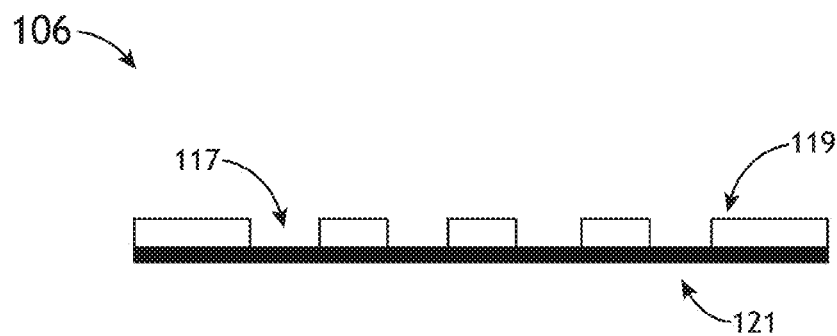
FIG. 1B is a schematic view of a membrane-type aperture element, in accordance with one embodiment of the present disclosure.
Figure 1C:
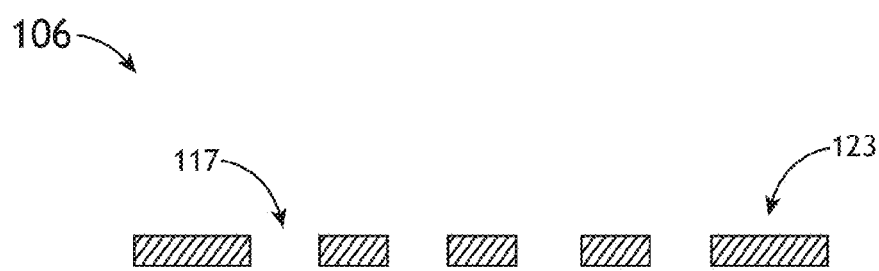
FIG. 1C is a schematic view of a grating-type aperture element, in accordance with one embodiment of the present disclosure.

FIGS. 1A-1C illustrate a system 100 equipped with an electron beam (e-beam) detection assembly 101, in accordance with one or more embodiments of the present disclosure. It is noted that the electron-optical system 100 may be utilized for any electron-optical application known in the art. For example, the system 100 may include an electron-optical sub-system 102 for generating one or more electron beams 104 and carrying out one or more electron-beam based applications. For example, the electron-optical sub-system 102 may be configured as, but is not limited to, an e-beam lithography tool. By way of another example, the electron-optical sub-system 102 may be configured as, but is not limited to, an e-beam inspection or review tool.

In one embodiment, the electron beam detection assembly 101 includes a first aperture element 106, a second aperture element 107, a scintillator element 108, an optical guide assembly 103 and a light detector 112. In one embodiment, as a stage assembly 116 scans the detection assembly 101 relative to the electron beam 104 emitted by the electron-optical sub-system 102, the e-beam 104 may pass through one or more of the aperture holes of the first aperture element 106 and second aperture element 107. In turn, this causes an excitation in the scintillator element 108, which leads to the generation of a light signal 110. The light 110 from the scintillator element 108 is then transferred to the light detector 112 via optical guide assembly 103 leading to a detection event. Based on this detection event, a controller 114 in communication with the light detector 112 may determine the position of the e-beam 104 associated with the electron-optical sub-system 102. In turn, the controller 114 may provide one or more adjustment instructions to one or more components of the electron-optical sub-system 102. In one embodiment, the controller 114 of detection assembly 101 includes one or more processors (not shown) configured to execute program instructions stored on a memory medium (not shown). In this regard, the one or more processors of controller 114 may carry out any of the various process steps of the present disclosure. The remainder of this disclosure will describe various embodiments of the electron-optical system 100.

In one embodiment, a sample (not shown) is secured by sample stage 116. For example, the sample may include, but is not limited to, a semiconductor substrate (e.g., semiconductor wafer).

The electron-optical sub-system 102 is suitable for generating one or more electron beams 104 in any manner known in the art. In one embodiment, the electron-optical sub-system 102 is configured to form a patterned e-beam. For example, the patterned e-beam may be generated so as to form lines or dots on a surface of a sample. In this regard, the patterned e-beam itself may include multiple electron beams arranged in lines or dots (or any other geometrical configuration). It is noted herein that patterned e-beam is not limited to lines or dots, which are provided merely for illustrative purposes. The formation of a patterned electron beam is described in U.S. Pat. No. 8,692,204 to Kojima et al., issued on Apr. 8, 2014, which is incorporated above by reference in the entirety.

In one embodiment, the e-beam detection assembly 101 may be utilized to measure one or more characteristics of the e-beam 104 during the use of system 100 for lithography and/or inspection processes. For example, the detection assembly 101 may be utilized, but is not required to be utilized, for measuring a position of the beam 104 during and/or between lithography and/or inspection processes.

In one embodiment, the e-beam detection assembly 101 includes a first aperture element 106 including a first set of apertures (e.g., apertures 117 in FIG. 1B or 1C). In one embodiment, the first set of apertures 117 of the first aperture element 106 are arranged in a selected pattern. It is noted herein that the implementation of the first aperture element 106 may serve to maintain or improve e-beam contrast at the plane of the first aperture element 106. In another embodiment, in the context of a patterned e-beam, the first set of apertures may be arranged in a pattern corresponding with the pattern (or the nominal pattern) of the patterned electron beam. The configuration of an aperture element having a set of apertures corresponding with the pattern of an e-beam is described in U.S. Pat. No. 8,692,204 to Kojima et al., issued on Apr. 8, 2014, which is incorporated above by reference in the entirety.

In another embodiment, the e-beam detection assembly 101 includes a second aperture element 107. In another embodiment, the second aperture element also includes a set of apertures. It is noted herein that the implementation of the second aperture element 107 may serve to strengthen the e-beam contrast at the plane of the second aperture element 107. For example, the apertures of the second aperture element 107 may be arranged to match the patterned arrangement of the apertures of the first aperture element 106. In this regard, the apertures of the second aperture element 107 correspond with the apertures of the first aperture element 106. In another embodiment, in the context of a patterned e-beam, both the apertures of the first aperture element 106 and the apertures of the second aperture element 107 correspond with the pattern arrangement (or the nominal pattern arrangement) of the patterned electron beam.

It is noted that the present disclosure is not limited to two aperture elements as described above and depicted in FIG. 1A, which are provided for illustrative purposes only. It is recognized herein that the system 100 may operate with a single aperture element, either the first aperture element 106 or the second aperture element 107. Further, the system 100 may utilize additional aperture elements beyond the first aperture element 106 and the second aperture element 107 to further improve e-beam contrast.

In one embodiment, as shown in FIG. 1B, the first aperture element 106 includes a set of membrane-based apertures 117. In one embodiment, the first aperture element 106 includes a stencil 119, with a membrane 121 that serves to support the stencil 119 in the pattern forming region of the stencil 119. In this regard, the stencil 119 includes a set of stencil apertures 117, or stencil holes, formed across at least a portion of the membrane 121. In one embodiment, the membrane 121 is formed from a material having high thermal conductivity. In one embodiment, the membrane 121 is formed from silicon or a silicon-based material (e.g., SiN). It is noted that the membrane 121 may be formed from any suitable low-Z material known in the art. In another embodiment, the membrane 109 is formed from a heavy metal, such as, but not limited to, chromium or tungsten. The thickness of the membrane 121 may depend on the material used for the membrane 121 and the structure of the stencil 119, with the membrane 121 being thick enough to provide adequate support to the stencil 119 features used for e-beam patterning. Further, the membrane 121 should be thin enough such that it is transparent or at least semi-transparent to the electron beam 104. For example, the membrane 121 may have a thickness of 1-5 µm.

In another embodiment, the stencil 119 is formed from a high-Z material. For example, the stencil 119 may be formed from molybdenum or platinum. The thickness of the stencil 119 may depend on the material used for the stencil 119 and the energy of the electron beam 104 and should have a thickness to provide sufficient scattering of the electron beam 104. For example, the stencil 119 may have a thickness of approximately 1-10 µm.

In another embodiment, as shown in FIG. 1C, the first aperture element 106 includes a metal grating structure 123. In this regard, the metal grating structure 123 includes a set of apertures 117. The metal grating structure 123 may be formed from any suitable material known in the art. For example, the metal grating structure 123 may be formed from, but is not limited to, tungsten, molybdenum or platinum.

It is further noted that the second aperture element 107 may be formed in any manner applicable to the first aperture element 106 noted above. For example, the second aperture element 107 may include a stencil/membrane assembly, as depicted in FIG. 1B. By way of another example, the second aperture element 107 may include a metal grating structure, as depicted in FIG. 1C.

Aperture assembly structures suitable for e-beam detection are described in detail in U.S. Pat. No. 8,692,204 to Kojima et al., issued on Apr. 8, 2014, which is incorporated above by reference in the entirety.

Referring again to FIG. 1A, in one embodiment, the scintillator element 108 is configured to receive electrons of the electron beam 104 transmitted through the first aperture element 106 and the second aperture element 107 and generates light signal 110. For example, the scintillator element 108 may include a layer of scintillating material. The scintillator element 108 may include any scintillating material known in the art. For example, the scintillator element 108 may include, but is not limited to, a single crystal of Yttrium-aluminum-garnet (YAG) plate. The scintillator element 108 converts electrons of the patterned electron beam 104 that impinge on the scintillator element 108 into photons, forming the light signal 110. It is noted herein that the conversion of the electrons of the patterned electron beam 104 to a light signal 110 via the scintillator element 108 serves to mitigate the impact of magnetic and electric fields associated with other portions (e.g., magnetic stages) of system 100.

In one embodiment, the light detector 112 is configured to detect at least a portion of the light signal 110 emitted by the scintillator element 108. In one embodiment, the light detector 112 is a position-sensitive light detector. As noted previously herein, in the case of a single beam being transmitted through one aperture of the first and second aperture elements 106, 107, the position of the beam 104 may be determined by correlating the light signal 110 with the position of the e-beam detection assembly 101 (specifically the aperture elements 106,107) as the detection assembly 101 is scanned relative to the e-beam 104. In another embodiment, the light detector 112 may be configured for position detection in the context of a patterned beam. In the case of a patterned beam, the combination of the pitched of the aperture elements 106, 107 and the patterned beam may result in a Moire pattern formed at the light detector 112, which may be used to determine alignment of the patterned beam. The determination of alignment of a patterned beam is described in detail in U.S. Pat. No. 8,692,204 to Kojima et al., issued on Apr. 8, 2014, which is incorporated above by reference in the entirety.

In one embodiment, the light detector 112 may include any light detector known in the art suitable that is position-sensitive. For example, the light detector 112 may include, but is not limited to, a photomultiplier tube (PMT). By way of another example, the light detector 112 may include, but is not limited to, a multi-channel PMT. By way of another example, the light detector 112 may include, but is not limited to, a diode sensor (e.g., silicon diode sensor). By way of another example, the light detector 112 may include, but is not limited to, a segmented diode sensor (e.g., segmented silicon diode sensor). By way of another example, the light detector 112 may include, but is not limited to, multiple diode sensors. By way of another example, the light detector 112 may include, but is not limited to, a charge-coupled device (CCD).

In one embodiment, the e-beam detection assembly 101 includes an optical guide assembly 103. In one embodiment, the optical guide assembly 103 is configured to direct the light signal 110 generated by the scintillator element 108 to the light detector assembly 112. In one embodiment, the optical guide assembly 103 is disposed on the sample stage 116 and arranged to guide the light signal 110 from the scintillator element 108 to the light detector 112. In another embodiment, the optical guide assembly 103 is configured to transmit the light signal 110 to the light detector 112 via free space coupling. In this regard, upon exiting the output portion of the optical guide assembly 103, light signal 110 from the scintillator element 108 traverses free space and impinges on the light detector 112.

Various forms of the optical guide assembly 103 are described throughout the remainder of this disclosure.

In one embodiment, the electron beam detection assembly 101 may provide feedback and/or calibration control of the electron-optical sub-system 102. In one embodiment, the electron beam detection assembly 101 includes a controller 114. In another embodiment, the controller 114 is communicatively coupled to the light detector 112 and is configured to receive one or more measurements from the light detector 112. In another embodiment, the controller 114 is also coupled to one or more portions of the electron-optical sub-system 102 (e.g., electron source, electron-optics and the like). In this regard, in response to one or more measurements from the light detector 112 (e.g., beam position measurements), the controller 114 may adjust a condition of one or more components of the electron-optical sub-system 102.

It is noted herein that the electron-optical sub-system 102 may include any set of components known in the art of electron-optical tools. As noted previously herein, the electron-optical sub-system 102 may be configured as an e-beam lithography tool, such as a reflective e-beam lithography tool. In addition, the electron-optical sub-system 102 may be configured as an e-beam inspection or review tool. For example, the electron-optical sub-system 102 may include, but is not limited to, an electron source (e.g., electron gun), a pattern generator (e.g., DPG, aperture plate and the like), illumination optics, projection optics, beam steering optics and the like. In this regard, the controller 114 may provide adjustment instructions to any one of the components of the electron-optical sub-system 102 in response to one or more measurements from the light detector 102 outside of a desired threshold. For example, in response to a position measurement of one or more e-beams 104 of the electron-optical sub-system 102 by light detector 112, the controller 114 may adjust one or more components of the electron-optical sub-system 102. For example, the controller 114 may adjust one or more beam steering coils of the electron-optical sub-system 102 in order to adjust the position of the e-beam 104 (or portions of beam in the case of a patterned beam). For instance, the controller 114 may adjust one or more beam steering coils of the electron-optical sub-system 102 in order to adjust the position of the e-beam 104.

In another embodiment, the electron beam detection assembly 101 may provide feedback and/or calibration control of the electron-optical sub-system 102 in order to adjust any operating condition of the electron-optical sub-system 102 known in the art. For example, the controller 114 may provide adjustment instructions to one or more components of the electron-optical sub-system 102 in order to adjust the focus, astigmatism, scaling, rotation, skew and center position of the e-beam 104 generated by the electron-optical sub-system 102. By way of another example, the controller 114 may provide adjustment instructions to one or more components of the electron-optical sub-system 102 in order to adjust the projection field of the e-beam 104 generated by the electron-optical sub-system 102.

In another embodiment, the calibration and/or feedback provided by the pattern electron beam detection assembly 101 may be provided in real-time or near real-time to one or more components of the electron-optical sub-system 102.

In one embodiment, the sample stage 116 includes any sample stage suitable for use in the context of an electron-optical system. In one embodiment, the sample stage 116 includes set of stacked sub-stages. For example, the sample stage 116 may include, but is not limited to, a short-stroke linear stage 115 and a mechanical stage 117. In another embodiment, the short-stroke linear stage 115 may be levitated (e.g., magnetically levitated) above the mechanical stage 117. In this regard, the short-stroke linear stage 115 may be configured for floating above the mechanical stage 117 and being linearly translated above the mechanical stage 117. In another embodiment, the sample stage 116 along with the electron-optical sub-system 102 and e-beam detection assembly 101 may be housed in a vacuum chamber (e.g., see FIG. 1F).

Referring now to FIG. 1D, in one embodiment, the optical guide assembly 103 includes a light guide element 124. In one embodiment, the light guide element 124 is disposed on the sample stage 116 and arranged to guide light from the scintillator element 108 to the light detector 112. For example, the light guide element 124 may include any light guide element known in the art. For instance, the light guide element 124 may include, but is not limited to, a light pipe, one or more optical fibers and the like. The light guide element 124 may be formed from any material known in the art suitable for guiding light. For instance, the light guide element 124 may be formed from an organic material or an inorganic material.

In one embodiment, the light guide element 124 includes a collection element configured to collect light 110 emitted by the scintillator element 108 and direct the light towards the light detector 112. In another embodiment, the light guide element 124 includes a collimator 105. For example, the collimator 105 may collimate light 110 from the scintillator element 108 as it exits the light guide element 124 of the optical guide assembly 103.

In another embodiment, the light guide element 124 is configured to transmit light 110 to the light detector 112 via free space coupling. In this regard, upon exiting the output portion of the light guide element 124 light 110 from the scintillator element 108 traverses free space and impinges on the light detector 112.

In another embodiment, the light guide element 124 includes a reflective external coating (not shown). The reflective external coating serves to improve the transfer efficiency of light from the input of the light guide element 124 to the output of the light guide element 124 by reducing leakage along the light guide element 124.

Figure 1E:
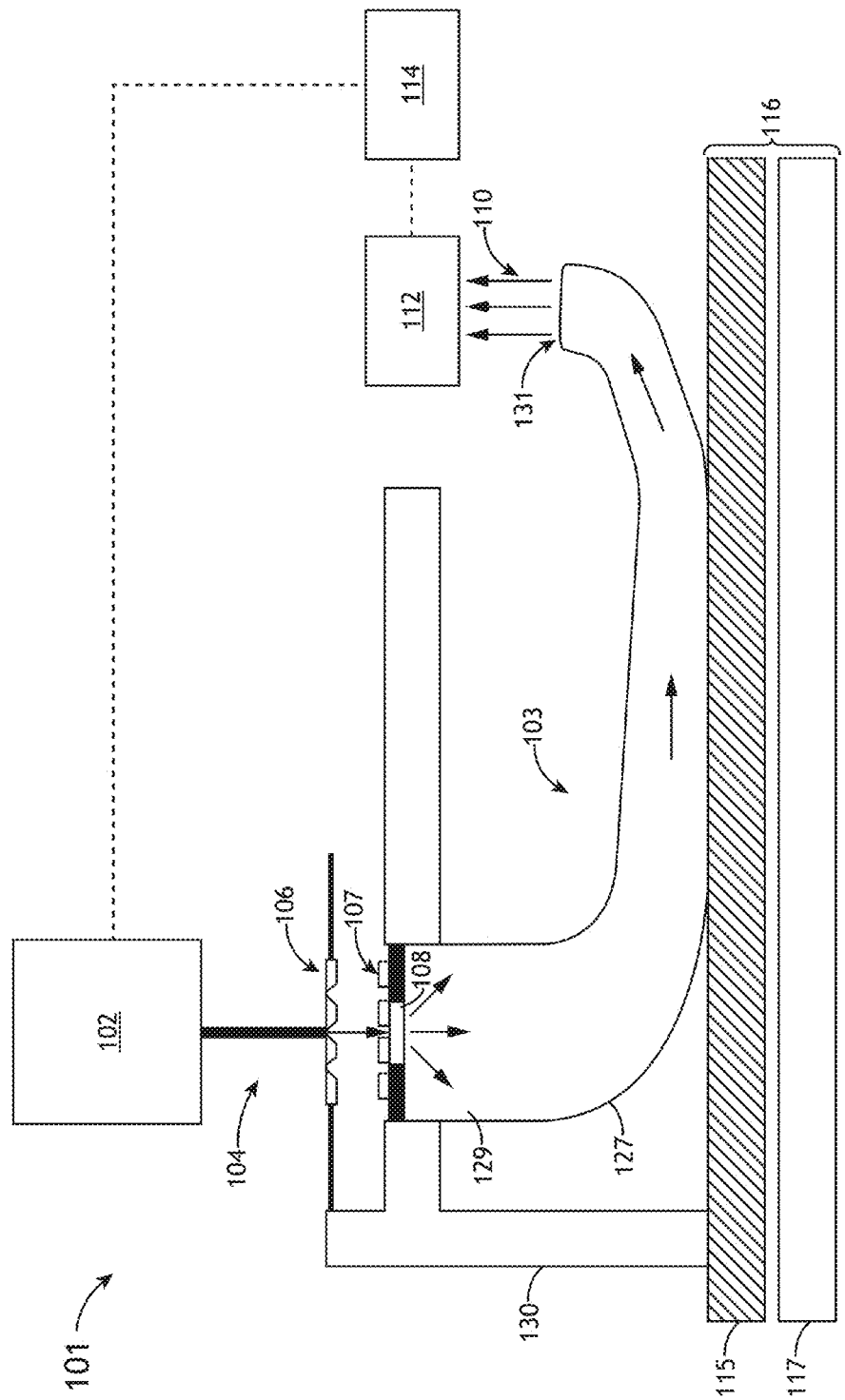
FIG. 1E is a schematic view an electron beam detection assembly, in accordance with one embodiment of the present disclosure.

FIG. 1E illustrates a light pipe 127 suitable for use as the optical guide assembly 103 of the patterned e-beam detection assembly 101, in accordance with another embodiment of the present disclosure. In one embodiment, the light pipe 127 is configured to collect light from the scintillator element 108. In one embodiment, the light pipe 127 has a plano optical entrance portion 129. In another embodiment, the light pipe 127 has a non-plano optical entrance portion (not shown). In one embodiment, the light pipe 127 has a plano optical exit portion 131. In another embodiment, the light pipe 127 has a non-plano optical exit portion (not shown).

In one embodiment, the entrance portion 129 of the light pipe 127 may be positioned at least proximate to the scintillator element 108. For example, as shown in FIG. 1E, the entrance portion 129 of the light pipe 127 may be, but is not required to be, directly coupled to the scintillator element 108. For instance, a scintillating material may be formed directing on the surface of the entrance portion 129 of the light pipe 127. By way of another example, not shown in FIG. 1E, the entrance portion 129 of the light pipe 127 may be, but is not required to be, positioned some distance from the scintillator element 108 such that light from the scintillator element 108 traverses free space prior to entering the entrance portion 129 of the light pipe 127.

In another embodiment, the exit portion 131 of the light pipe 127 may be positioned at least proximate to the light detector 112. For example, although not shown, the exit portion 131 of the light pipe 127 may be, but is not required to be, directly coupled to the light detector 112. By way of another example, as shown in FIG. 1E, the exit portion 131 of the light pipe 127 may be, but is not required to be, positioned some distance from the light detector 112 such that light 110 from the scintillator element 108 traverses free space after exiting the light pipe 127 and prior to impinging on the light detector 112.

It is noted herein that the light pipe 127 may take on any form and is not limited to the configuration depicted in FIG. 1E, which is provided merely for illustrative purposes. As such, the light pipe 127 may take on any shape, allowing the light pipe 127 to deliver light 110 from the scintillator element 108 to the light detector 112 as desired. It is noted herein that the light guide element 124 of the present disclosure is not limited to the light pipe 127, which is provided as one illustrative example. For example, rather than a light pipe 127, the light guide element 124 may include an optical fiber or bundle of optical fibers used to couple the light 110 from the scintillator element 108 to the light detector 112.

In another embodiment, the detection assembly 101 may include a support structure 130 for securing the components of the detection assembly 101 at or above the sample stage 116.

Figure 1F:
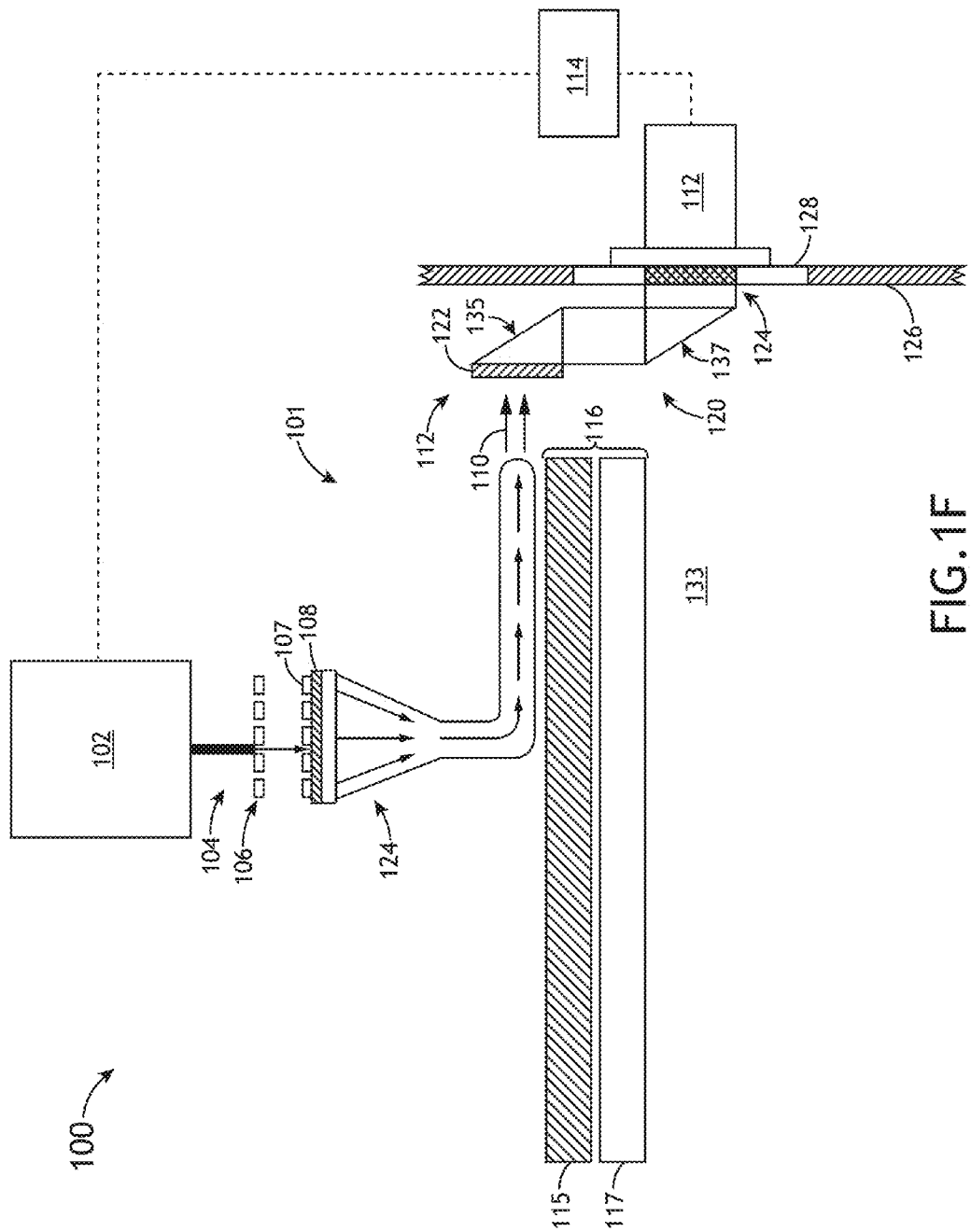
FIG. 1F is a schematic view an electron beam detection assembly, in accordance with one embodiment of the present disclosure.

FIG. 1F illustrates an optical receiver assembly 120 for transmitting light 110 from output of the optical guide assembly 103 to the light detector 112 in cases where the light detector 112 is positioned outside of vacuum chamber 133, in accordance with one or more embodiments of the present disclosure. In one embodiment, the optical receiver assembly 120 is disposed on a wall 126 of the vacuum chamber 133 and optically traverses the wall 126 of the vacuum chamber 133.

In one embodiment, the optical receiver assembly 120 includes one or more optical components (e.g., mirrors, prisms, light guides and etc.) for receiving light 110 from an exit portion 137 of the light guide element 124 and directing the light 110 through window 128 and to the light detector 112. For example, as shown in FIG. 1F, the optical receiver assembly 120 have a periscope configuration, whereby a pair of mirrors 135 (or prisms) direct the light 110 from the entrance of the optical receiver assembly 120 to the light detector 112. It is noted herein that the periscope configuration of the optical receiver assembly 120 depicted in FIG. 1F is not limiting and is provided merely for illustrative purposes. It is recognized herein that the optical receiver assembly 120 may be constructed in any form suitable for directing light 110 from the entrance of the optical receiver assembly 120 to the light detector 112.

In another embodiment, the optical receiver assembly 120 may include one or more material coatings. In one embodiment, the entrance portion 135 and/or exit portion 137 of the optical receiver assembly 120 may be coated with one or more coatings. For example, as shown in FIG. 1F, the entrance face of the optical receiver assembly 120 may be, but is not required to be, coating with an anti-reflection (AR) coating. In another embodiment, the exit portion 137 of the optical receiver assembly 120 or the window 128 of vacuum chamber 133 may be fitted with a filter (e.g., band-pass filter).

While the optical receiver assembly 120 is depicted in conjunction with the light guide assembly 124, it is noted herein that the optical receiver assembly 120 may be implemented within the context of any of the optical guide assembly 103 configurations disclosed herein. In this regard, the optical receiver assembly 120 may be utilized to transfer light from within the vacuum chamber 133 to an outside light detector 112 in any of the optical guide assembly 103 embodiments depicted in FIGS. 1A-3.

Figure 1G:
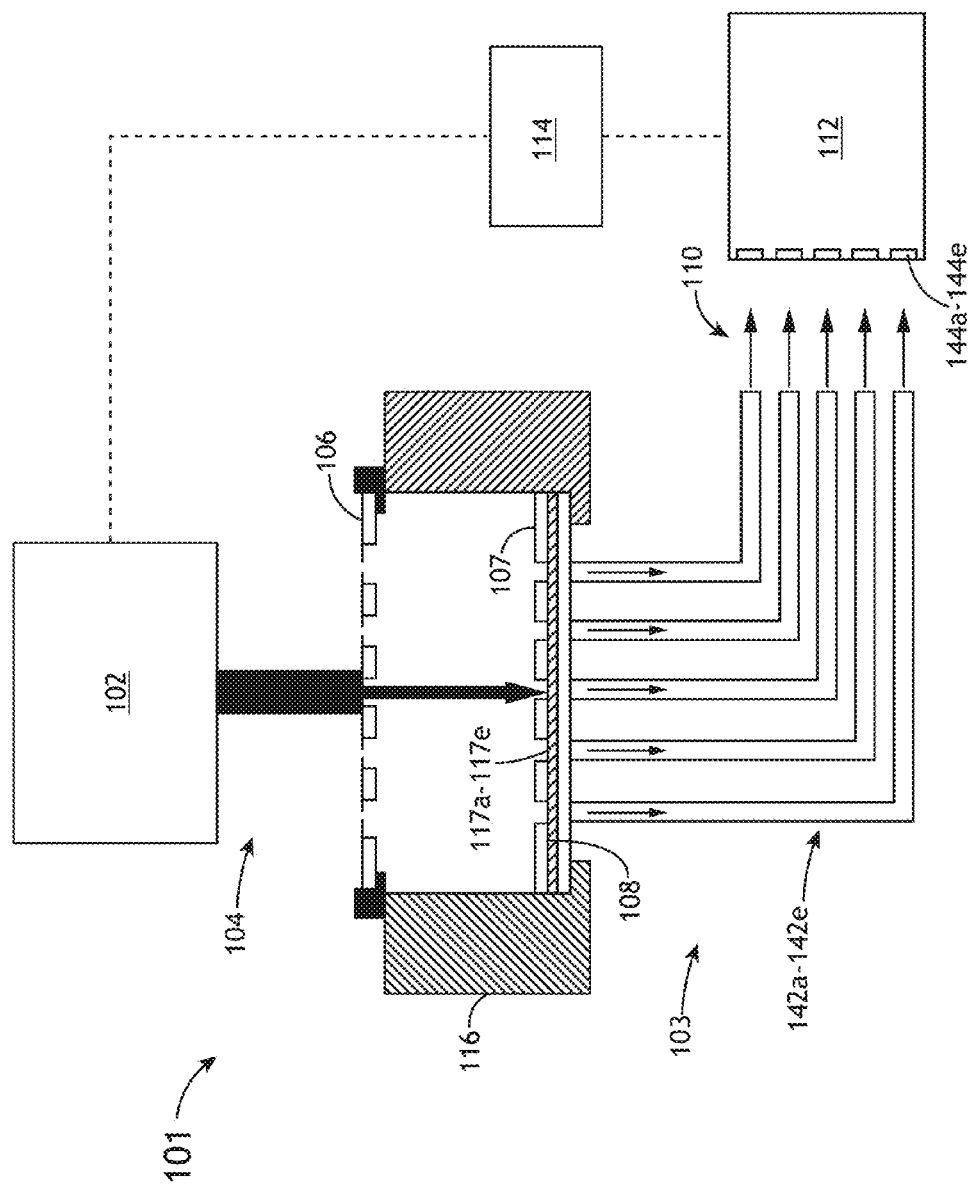
FIG. 1G is a schematic view an electron beam detection assembly, in accordance with one embodiment of the present disclosure.

Referring now to FIG. 1G, in one embodiment, the optical guide assembly 103 includes multiple light guide elements 142a-142e. In one embodiment, the light guide elements 142a-142e are disposed on the sample stage 116 (not shown in FIG. 1G) and are arranged to guide light 110 from the scintillator element 108 to the light detector 112 (or light detectors).

In one embodiment, each of the light guide elements 142a-142e may be individually optically coupled to a single aperture of the second aperture element 107. In this regard, light from each aperture 117a-117e of the second aperture element 107 is directed to the detector 112 through a dedicated light guide element 144a-144e. In another embodiment, the light detector 112 may include multiple detection channels 144a-144e. In such a configuration, the combination of the dedicated light guide elements 142a-142e and the dedicated detection channels 144a-144e allows the detector 112 to detect light from the scintillator element 108 on an aperture-by-aperture basis. As the e-beam detection assembly 101 is scanned relative to the e-beam 104 of the electron-optical sub-system 102 the position of the e-beam 104 may be determined by the activation of one of the detection channels 144a-144e of the light detector 112.

It is noted here in that the light guide elements 142a-142e may include any light guide elements known in the art. For example, one or more of the light guide elements 142a-142e may include, but are not limited to, an optical fiber. For instance, the light guide elements 142a-142e may include an optical bundle with each fiber (or groups of fibers) serving to couple a single aperture (e.g., 117a, 117b, 117c, 117d or 117e) to a single channel (e.g., 144a, 144b, 144c, 144d or 144e) of the light detector 112.

By way of another example, one or more of the light guide elements 142a-142e may include, but are not limited to, a light pipe. For instance, the light guide elements 142a-142e may include a set of light pipes with each light pipe serving to couple a single aperture (e.g., 117a, 117b, 117c, 117d or 117e) to a single channel (e.g., 144a, 144b, 144c, 144d or 144e) of the light detector 112.

In another embodiment, rather than a multi-channel light detector, it is recognized herein that an analogous configuration may be accomplished utilizing multiple individual light detectors 112 (not shown). It is noted herein that, while the configuration of FIG. 1G is depicted as passing through the sample stage 116, this configuration should not be interpreted as a limitation on the present disclosure. It is recognized herein that an equivalent configuration may be accomplished utilizing a support structure (e.g., similar to support structure 130 in FIG. 1H).

Figure 1H:
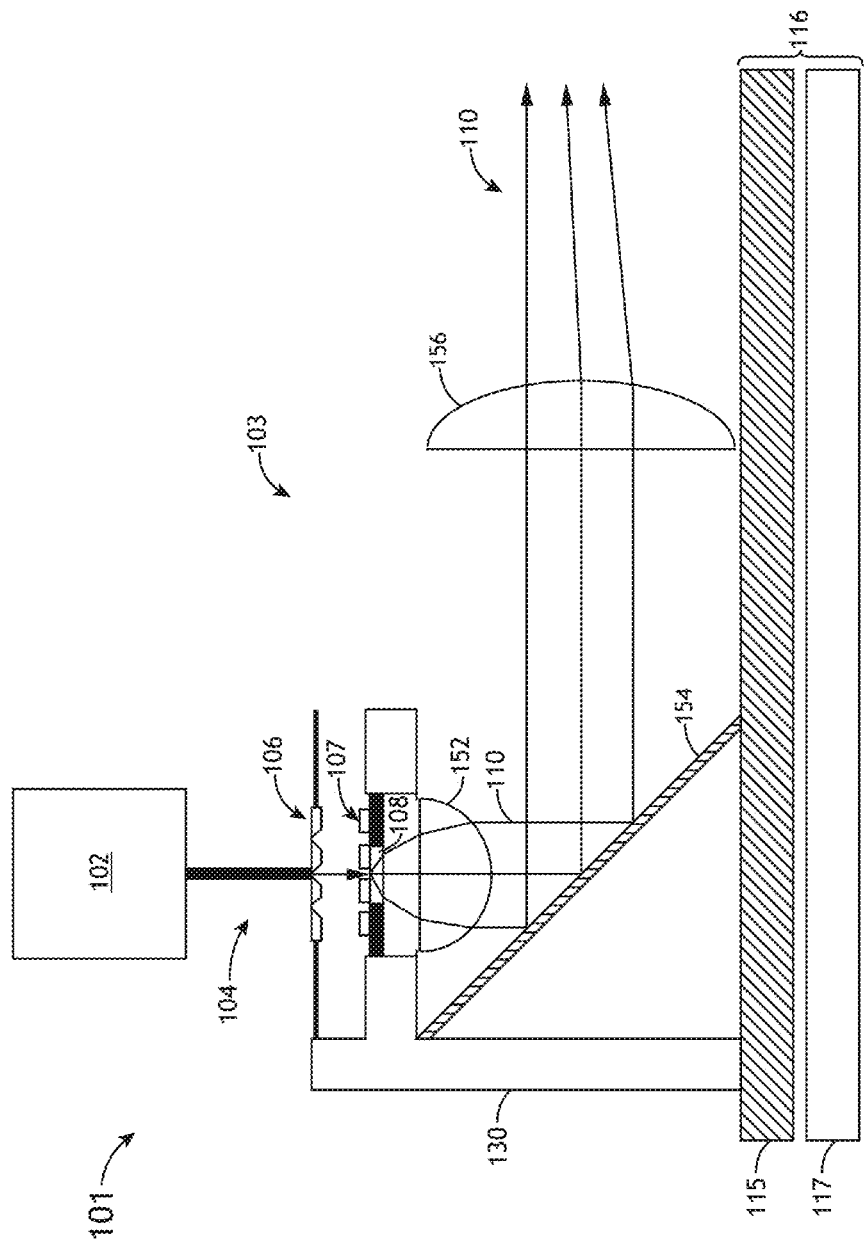
FIG. 1H is a schematic view an electron beam detection assembly, in accordance with one embodiment of the present disclosure.
Figure 1I:
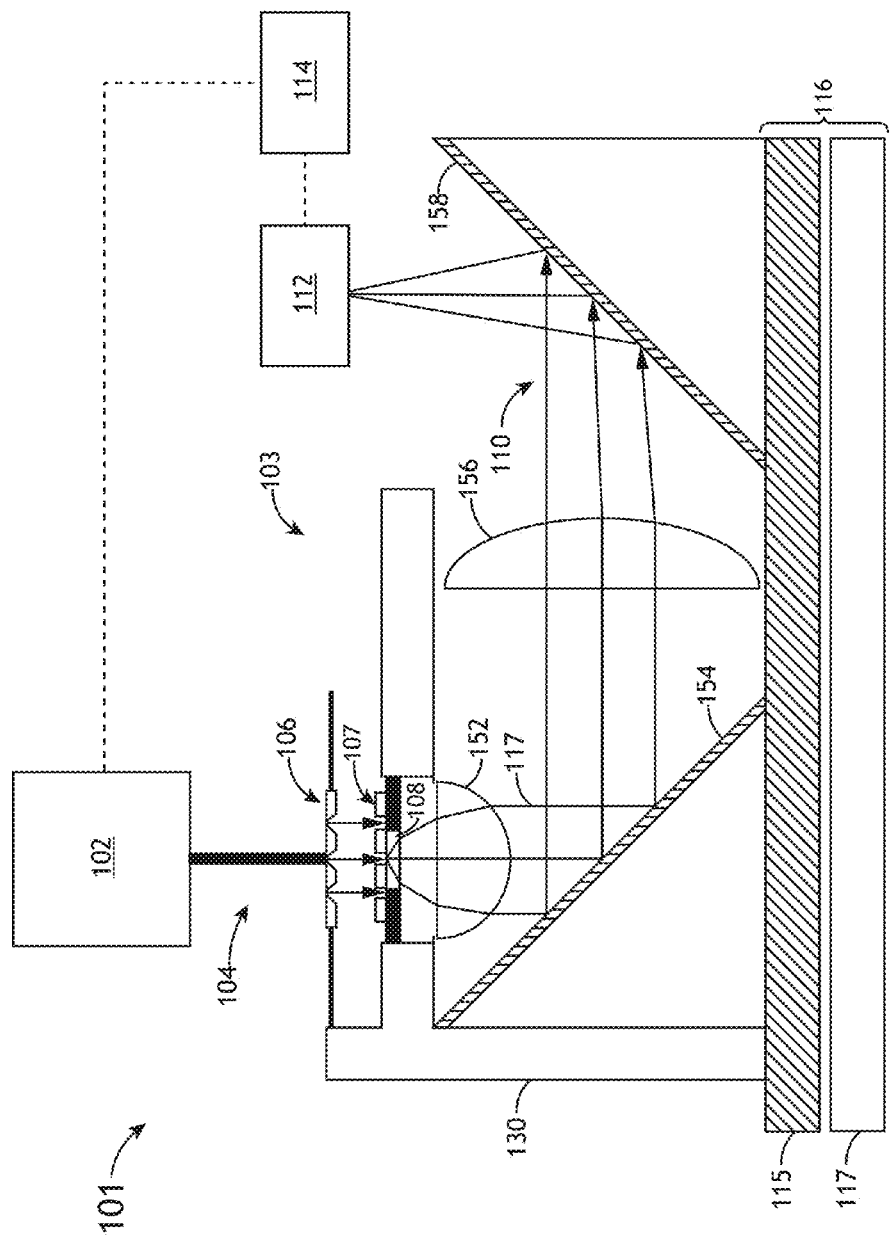
FIG. 1I is a schematic view an electron beam detection assembly, in accordance with one embodiment of the present disclosure.

Referring now to FIGS. 1H-1I, in one embodiment, the optical guide assembly 103 includes one or more mirrors and/or one or more lenses for directing and focusing light 110 from the scintillator 108 onto the light detector 112. In one embodiment, the optical guide assembly 103 includes a collimating lens 152 configured to receive light 110 from the scintillator element 108 and then collimate the light 110. In another embodiment, the optical guide assembly 103 includes a mirror 154 for directing the collimated beam toward the light detector 112 (not show in FIG. 1H). In another embodiment, the optical guide assembly 103 includes a focusing lens 156 for focusing the collimated beam of light onto the light detector 112. In another embodiment, as shown in FIG. 1I, the optical guide assembly 103 includes an additional mirror 158 for directing the focused beam from focusing lens 156 to the light detector 112. In one embodiment, mirror 154 and/or mirror 156 of the optical guide assembly 103 are planar mirrors.

Referring now to FIG. 1J, in one embodiment, the optical guide assembly 103 includes one or more curved mirrors 160, 162 for directing and focusing light 110 from the scintillator 108 onto the light detector 112. For example, the first curved mirror 160 may collect and collimate the light 110 from the scintillator element 108. Then, the curved mirror 160 may direct the light 110 to a second curved mirror 162. The second curved mirror 162 may then reflect and focus the light 110 onto the light detector 112. The curved mirrors 160, 162 may take on any shape known in the art. For example, curved mirror 160 and/or curved mirror 162 may have, but is not required to have, one of the following shapes: spherical, parabolic, or aspherical. It is noted herein that this configuration is not limiting and is provided merely for illustrative purposes. For example, the second mirror 162 of this embodiment may be replaced with a focusing mirror, which may be used to focus light 110 from the first mirror 160 onto the light detector 112.

In another embodiment, as shown in FIG. 1K, the optical guide assembly 103 may include a lens array 170. For example, the lens array 170 may be used in combination with the first curved mirror 160 to collect and collimate light 110 from the scintillator element 108.

FIG. 2 illustrates an e-beam detection assembly 201 of system 100, in accordance with one or more embodiments of the present disclosure. As shown in FIG. 2, the e-beam detection assembly 201 includes a scattering element 207. In one embodiment, the scattering element 207 includes a set of pillar or rod structures 203 embedded in a substrate 205. The pillar structures 200 are selected such that they readily scatter electrons. In one embodiment, the pillar structures 203 are sub-micron in size. For example, the pillar structures 203 may be formed from a metal, such as a heavy metal. In another embodiment, the pillar structures 203 are formed in substrate 205 including a volume of low density material suitable for transmitting electrons. In one embodiment, as the e-beam detection assembly 201 is scanned across the e-beam 104 such that the e-beam 104 impinges on one of the pillars 203, the pillar 203 scatters electrons. In another embodiment, the scintillator element 108 then receives the scattered electrons and, in response, generates a light signal 110, as depicted in FIG. 2. This light signal 110 may then be directed to the light detector 112 (not shown in FIG. 2) via the optical guide assembly 103. For example, as shown in FIG. 2, the optical guide assembly 103 may include a lens 204 for collecting light 110 and directing the light to downstream optical components of the optical guide assembly 103. It is noted herein that the various components of the optical guide assembly 103 and the e-beam detection assembly 101 (other than the aperture elements 106, 107) should be interpreted to extend to the embodiment depicted in FIG. 2.

In another embodiment, the electron detection assembly 201 includes a Faraday cup 202. In one embodiment, the Faraday cup 202 is arranged so as to collect a portion of the electrons scattered by one or more of the pillars 203. For example, the Faraday cup 202 may be aligned with a pass through hole in the scintillator element 108. In another embodiment, the electron detection assembly 201 includes a current meter 206 electrically coupled to the Faraday cup 202. In another embodiment, the current meter 206 is coupled to controller 114 (or another controller). In one embodiment, the controller 114 may then determine, or estimate, a number of electrons collected by the Faraday cup 202 based on the measure current from the Faraday cup 202. In this regard, the electron detection assembly 201 may simultaneously measure the light signal 110 at the light detector 112 and the electron capture events in the Faraday cup 202. This information may then be used to determine a position or alignment of the e-beam 104 using the processes described previously herein.

Figure 3A:
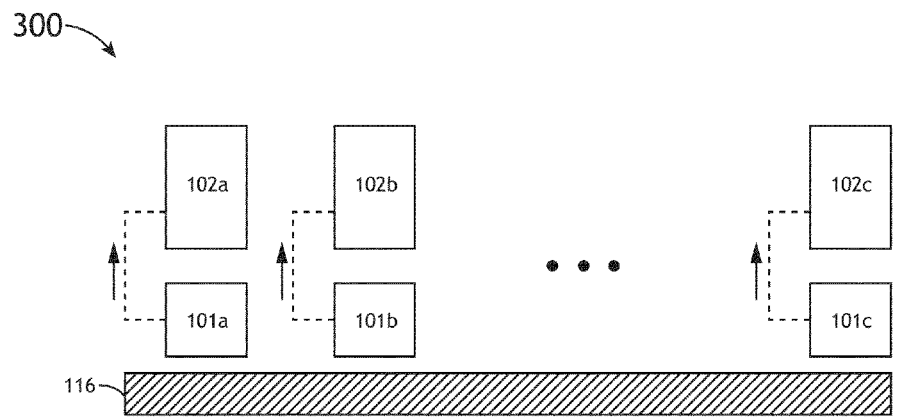
FIGS. 3A-3B are block diagram views of systems equipped with multiple electron beam detection assemblies, in accordance with one embodiment of the present disclosure.
Figure 3B:
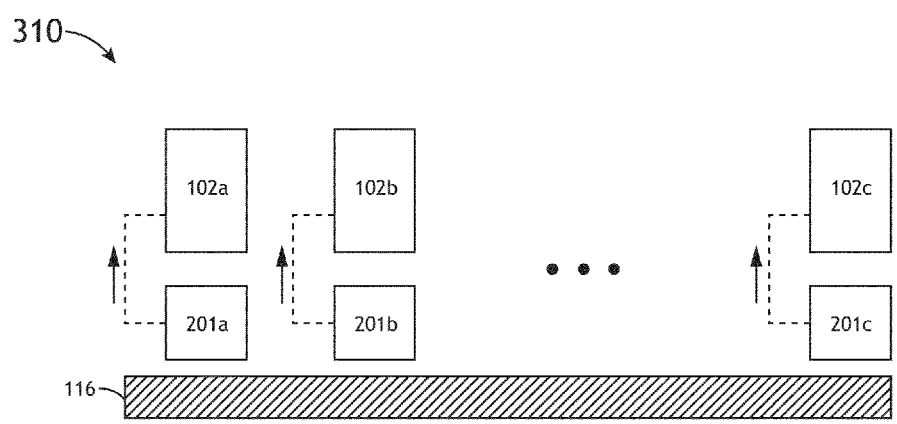

FIGS. 3A-3B illustrate systems 300 and 310 including multiple e-beam detection assemblies, in accordance with one or more embodiments of the present disclosure. In one embodiment, as shown in FIG. 3A, the system 300 includes multiple e-beam detection assemblies 101a-101c. For example, each of the detection assemblies 101a-101c may consist of an embodiment of the e-beam detection assembly 101 as described previously herein. In another embodiment, as shown in FIG. 3B, the system 310 includes multiple e-beam detection assemblies 201a-201c. For example, each of the detection assemblies 201a-201c may consist of an embodiment of the e-beam detection assembly 201 as described previously herein. It is noted herein that the sets of multiple e-beam detection assemblies 101a-101c and/or 201a-201c may be disposed on or near the sample stage 116 in parallel. This configuration allows for the measurement and/or calibration of multiple electron-optical sub-systems 102a-102c.

In another embodiment, the e-beam detection assemblies 101a-101c and/or 201a-201c may be formed in modules. In one embodiment, the e-beam detection assemblies 101a-101c and/or 201a-201c may be selectively mounted on (or removed from) the sample stage 116. Such a configuration allows the system 300 and/or system 310 to be configured to match the number of e-beam detection assemblies 101a-101c and/or 201a-201c to the number of electron-optical sub-systems 102a-102c.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

The invention claimed is:

1. An apparatus for electron beam detection comprising:
   a first aperture element including a first plurality of apertures;
   a second aperture element including a second plurality of apertures, the second plurality of apertures arranged in a pattern corresponding with the pattern of the first plurality of apertures;
   a scintillator element configured to receive electrons of the patterned electron beam transmitted through the first aperture element and the second aperture element, wherein the scintillator element is configured to generate light in response to the received electrons;
   an optical guide assembly; and
   a light detector configured to measure a light signal from the scintillator element, wherein the optical guide assembly is configured to direct light generated by the scintillator element to the light detector, at least a portion of a path defined by the optical guide assembly is parallel to a surface of a sample, wherein the light detector is positioned at an edge portion of the sample.

2. The apparatus of claim 1, further comprising:
   a controller configured to determine a position of the electron beam based on the light signal measured by the light detector.

3. The apparatus of claim 1, wherein the optical guide assembly comprises:
a light guide element configured to guide light generated by the scintillator element to the light detector.

4. The apparatus of claim 3, further comprising:
a collimator arranged at an output portion of the light guide and configured to collimate the light guided to the output portion of the light guide.

5. The apparatus of claim 4, wherein the light guide element is configured to transmit light from the output of the light guide to the light detector via free space coupling.

6. The apparatus of claim 1, wherein the optical guide assembly comprises:
a plurality of light guide elements, wherein each light guide element is optically coupled to an aperture of the second plurality of apertures.

7. The apparatus of claim 6, wherein each light guide element is configured to guide light from an aperture of the second plurality of apertures to one of a plurality of channels of the light detector.

8. The apparatus of claim 1, wherein the optical guide assembly comprises:
a first planar mirror; and
a second planar mirror, wherein the first planar mirror and the second planar mirror are arranged to direct the light from the scintillator element to the light detector.

9. The apparatus of claim 8, further comprising:
one or more lens elements.

10. The apparatus of claim 1, wherein the optical guide assembly comprises:
a first curved mirror; and
a second curved mirror, wherein the first curved mirror and the second curved mirror are arranged to direct the light from the scintillator element to the light detector.

11. The apparatus of claim 1, wherein the optical guide assembly is disposed on a sample stage.

12. The apparatus of claim 11, wherein the light detector is positioned proximate to an outside edge portion of the sample stage.

13. The apparatus of claim 11, wherein the sample stage is disposed within a vacuum chamber.

14. The apparatus of claim 13, further comprising:
an optical receiver assembly configured to receive light from the optical guide assembly and transmit the light through a window of the vacuum chamber and to the light detector, wherein the light detector is positioned outside of the vacuum chamber.

15. The apparatus of claim 1, wherein the electron beam is a patterned electron beam.

16. The apparatus of claim 1, wherein the light detector comprises:
a photomultiplier tube.

17. The apparatus of claim 1, wherein the light detector comprises:
a multi-channel photomultiplier tube.

18. The apparatus of claim 1, wherein the light detector comprises:
an array of photomultiplier tubes.

19. The apparatus of claim 1, wherein the light detector comprises:
a diode sensor.

20. The apparatus of claim 1, wherein the light detector comprises:
a segment diode sensor.

21. The apparatus of claim 1, wherein the light detector comprises:
a charge-coupled device detector.

22. An apparatus for electron beam detection comprising:
a scattering element including a plurality of pillar structures configured to scatter electrons of the electron beam;
a scintillator element configured to receive electrons scattered from the plurality of pillar structures of the scattering element, wherein the scintillator element is configured to generate light in response to the received scattered electrons;
an optical guide assembly; and
a light detector configured to measure a light signal from the scintillator element, wherein the optical guide assembly is configured to direct light generated by the scintillator element to the light, at least a portion of a path defined by the optical guide assembly is parallel to a surface of a sample, wherein the light detector is positioned at an edge portion of the sample.

23. The apparatus of claim 22, further comprising:
a controller configured to determine a position of the electron beam based on the light signal measured by the light detector.

24. The apparatus of claim 22, wherein the plurality of pillar structures are embedded in a substrate.

25. The apparatus of claim 22, wherein at least some of the pillar structures are formed from metal.

26. The apparatus of claim 22, further comprising:
a Faraday cup configured to collect electrons scattered from the plurality of pillar structures; and
a current meter electrically coupled to the Faraday cup and configured to determine a number of electrons collected by the Faraday cup based on the measured current from the Faraday cup.

27. The apparatus of claim 22, wherein the electron beam is a patterned electron beam.

28. An electron-optical system with patterned electron beam detection comprising:
an electron-optical sub-system configured to generate an electron beam;
a sample stage configured to secure a sample; and
an electron beam detection assembly disposed on the sample stage comprising:
a first aperture element including a first plurality of apertures;
a second aperture element including a second plurality of apertures, the second plurality of apertures arranged in a pattern corresponding with the pattern of the first plurality of apertures;
a scintillator element configured to receive electrons of the electron beam transmitted through the first aperture element and the second aperture element, wherein the scintillator element is configured to generate light in response to the received electrons;
an optical guide assembly; and
a light detector configured to measure a light signal from the scintillator element, wherein the optical guide assembly is configured to direct light generated by the scintillator to the light detector assembly.

29. The electron-optical system of claim 28, further comprising:
a controller configured to determine a position of the electron beam based on the light signal measured by the light detector, wherein the controller is further configured to adjust a position of the electron beam generate by the electron-optical sub-system based on the determined position of the electron beam.

30. The electron-optical system of claim 28, further comprising:

a vacuum chamber, wherein the sample stage is disposed within the vacuum chamber.

31. The electron-optical system of claim 28, wherein the sample stage comprises:
a short stroke linear stage and mechanical stage, wherein the short stroke linear stage is levitatable above the mechanical stage.

32. The electron-optical system of claim 28, wherein the electron-optical sub-system is configured as an electron beam inspection tool.

33. The electron-optical system of claim 28, wherein the electron-optical sub-system is configured as electron beam lithography tool.

34. The electron-optical system of claim 33, wherein the electron beam lithography system is configured as a reflective electron beam lithography (REBL) tool.

35. The electron-optical system of claim 28, wherein the patterned electron beam detection assembly further comprises:
a controller communicatively coupled to the light detector.

36. The electron-optical system of claim 35, wherein the controller is communicatively coupled to the electron-optical sub-system and is configured to adjust one or more components of the electron-optical sub-system in response to one or more measurements from the light detector.

37. The electron-optical system of claim 36, wherein the controller is configured to calibrate the electron-optical sub-system in response to one or more measurements from the light detector.

38. An electron-optical system with electron beam detection comprising:
an electron-optical sub-system configured to generate an electron beam;
a sample stage configured to secure a sample; and
an electron beam detection assembly disposed on the sample stage comprising:
a scattering element including a plurality of pillar structures configured to scatter electrons of the electron beam;
a scintillator element configured to receive electrons scattered from the plurality of pillar structures of the scattering element, wherein the scintillator element is configured to generate light in response to the received scattered electrons;
an optical guide assembly; and
a light detector configured to measure a light signal from the scintillator element, wherein the optical guide assembly is configured to direct light generated by the scintillator element to the light detector.

39. The electron-optical system of claim 38, further comprising:
a controller configured to determine a position of the electron beam based on the light signal measured by the light detector, wherein the controller is further configured to adjust a position of the electron beam generate by the electron-optical sub-system based on the determined position of the electron beam.

* * * * *